US00PP37761P2

(12) United States Plant Patent
Clarkson

(10) Patent No.: US PP37,761 P2
(45) Date of Patent: Oct. 13, 2026

(54) ***FRAGARIA* PLANT NAMED 'AP208'**

(50) Latin Name: ***Fragaria* x *ananassa***
Varietal Denomination: AP208

(71) Applicant: Graham Clarkson, Faversham (GB)

(72) Inventor: Graham Clarkson, Faversham (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 19/533,150

(22) Filed: Feb. 7, 2026

(30) Foreign Application Priority Data

Jan. 6, 2026 (QZ) ..... PBR 20260016

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./209, 208
CPC ..... A01H 5/08; A01H 5/00; A01H 6/7409; A01H 6/74
See application file for complete search history.

(56) References Cited

U.S. PATENT DOCUMENTS

PP37,208 P3 * 1/2026 Clarkson ..... A01H 6/7409 Plt./209

* cited by examiner

*Primary Examiner* — June Hwu
(74) *Attorney, Agent, or Firm* — Penny J. Aguirre

(57) ABSTRACT

A new cultivar of *Fragaria* plant named 'AP208' that is characterized by its fruit that are medium to large in size, conical in shape, and juicy, with a sweet flavor, its high fruit yields throughout the season and a good post-harvest shelf life, its fruit that are very firm, highly glossy, and medium red in color, its fruit that are very firm, highly glossy, and medium red in color, its fruit with an even surface texture and achenes that are primarily level with the surface, its leaves with no interveinal blistering and concave or straight in cross-section, its dense plants that are strong in vigor with an upright plant habit.

3 Drawing Sheets

Botanical classification: *Fragaria* x *ananassa.*
Variety denomination: 'AP208'.

CROSS-REFERENCE TO RELATED APPLICATIONS

This application claims priority to European Community Plant Variety Office (CPVO) Plant Breeder's Rights Application No. 2026/0016 filed on Jan. 6, 2026, under 35 U.S.C. 119(f), the entire contents of which is incorporated by reference herein. This application is also related to a plant breeders' rights application in The United Kingdom on Jan. 6, 2026, Application No. 10/229. The information for the plant breeders' rights applications was received directly from the Inventor.

BACKGROUND OF THE INVENTION

The present invention relates to a new and distinct cultivar of *Fragaria*, botanically known as *Fragaria* x *ananassa* 'AP208' and will be referred to hereafter by its cultivar name 'AP208'. 'AP208' is an everbearing strawberry plant primarily adapted to the climate and growing conditions of the United Kingdom and other regions of similar climate and day length for use in the fresh fruit market.

The new cultivar was derived from an ongoing breeding program conducted by the Inventor in Faversham, Kent, United Kingdom. The goal of the breeding program was to develop a new cultivar of *Fragaria* large fruit that is large with high yields, uniform shape, firm skin, good eating quality, and consistent cropping combined with good disease tolerance. 'AP208' arose from a controlled cross made by the Inventor in February of 2019 between an unpatented selection from the Inventor's breeding program, designated as accession number 'AB171' as the female parent and *Fragaria* 'Eves Delight 2' (U.S. Plant Pat. No. 32,418), as the male parent. 'AP208' was selected as a single unique plant in Faversham, Kent, United Kingdom in summer of 2020 from amongst the seedlings that resulted from the above cross.

Asexual propagation of the new cultivar was first accomplished by rooting stolons in Faversham, Kent, United Kingdom in summer of 2020. Asexual propagation by rooting of stolons and tissue culture using meristematic tissue has shown that the unique characteristics of the new cultivar are stable and reproduced true to type in successive generations.

SUMMARY OF THE INVENTION

The following traits have been repeatedly observed and represent the characteristics of the new cultivar. These attributes in combination distinguish 'AP208' as a unique cultivar of *Fragaria.*

1. 'AP208' exhibits fruit that are medium to large in size, conical in shape, and juicy, with a sweet flavor.
2. 'AP208' exhibits high fruit yields throughout the season and a good post-harvest shelf life.
3. 'AP208' exhibits fruit that are very firm, highly glossy, and medium red in color.

4. 'AP208' exhibits fruit with an even surface texture and achenes that are primarily level with the surface.
5. 'AP208' exhibits leaves with no interveinal blistering and concave or straight in cross-section.
6. 'AP208' exhibits dense plants that are strong in vigor with an upright plant habit.

The female parent of 'AP208' differs from 'AP208' in having smaller fruit that are darker red in color. The male parent of 'AP208' differs from 'AP208' in having fruit that are less sweet, less juicy, more acidic, lighter red in color, and less firm.

'AP208' can be compared to *Fragaria* cultivars 'Eves Joy' (U.S. Plant Pat. No. 35,911) and 'PGP182' (U.S. Pat. No. 37,208). 'Eves Joy' is primarily similar to 'AP208' in producing high fruit yields with a good post-harvest shelf life and fruit that is conical-shaped, highly glossy, sweet, and an even surface texture. 'Eves Joy' primarily differs from 'AP208' in having fruit that is larger in size, less firm skin, a lower Brix level, and achenes that are mostly below the fruit level. 'Eves Joy' also differs from 'AP208' in having a less dense canopy, a small plant size, and leaves that are glossy with some interveinal blistering. 'PGP182' is similar to 'AP208' in having fruit that is highly glossy and juicy and have a very good post-harvest shelf life. 'PGP182' differs from 'AP208' in having fruit with skin and flesh that is less firm, a stronger aroma, achenes that are mostly present below the fruit level, and slightly less acidic.

BRIEF DESCRIPTION OF THE DRAWINGS

The accompanying color photographs illustrate the overall appearance and distinct characteristics of the new *Fragaria*. The photographs were taken of 3-month-old plants (from a rooted cutting) of 'AP208' as grown on table-tops in coir bags under tunnels with polyethylene covers in Faversham, Kent, United Kingdom.

The photograph in FIG. 1 provides a view of plants of 'AP208' in bloom and bearing fruit.

Figure 1:
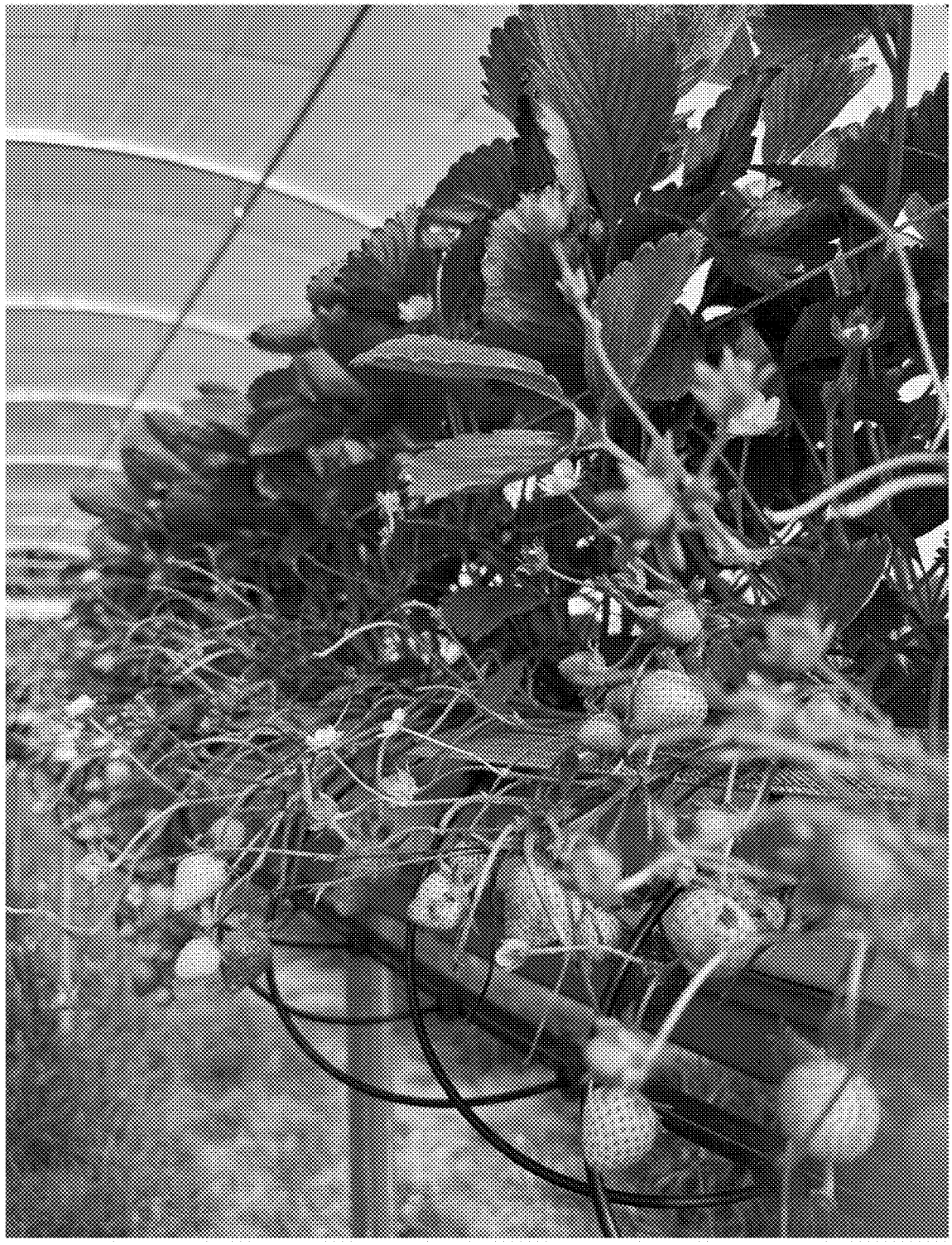
Figure 2:
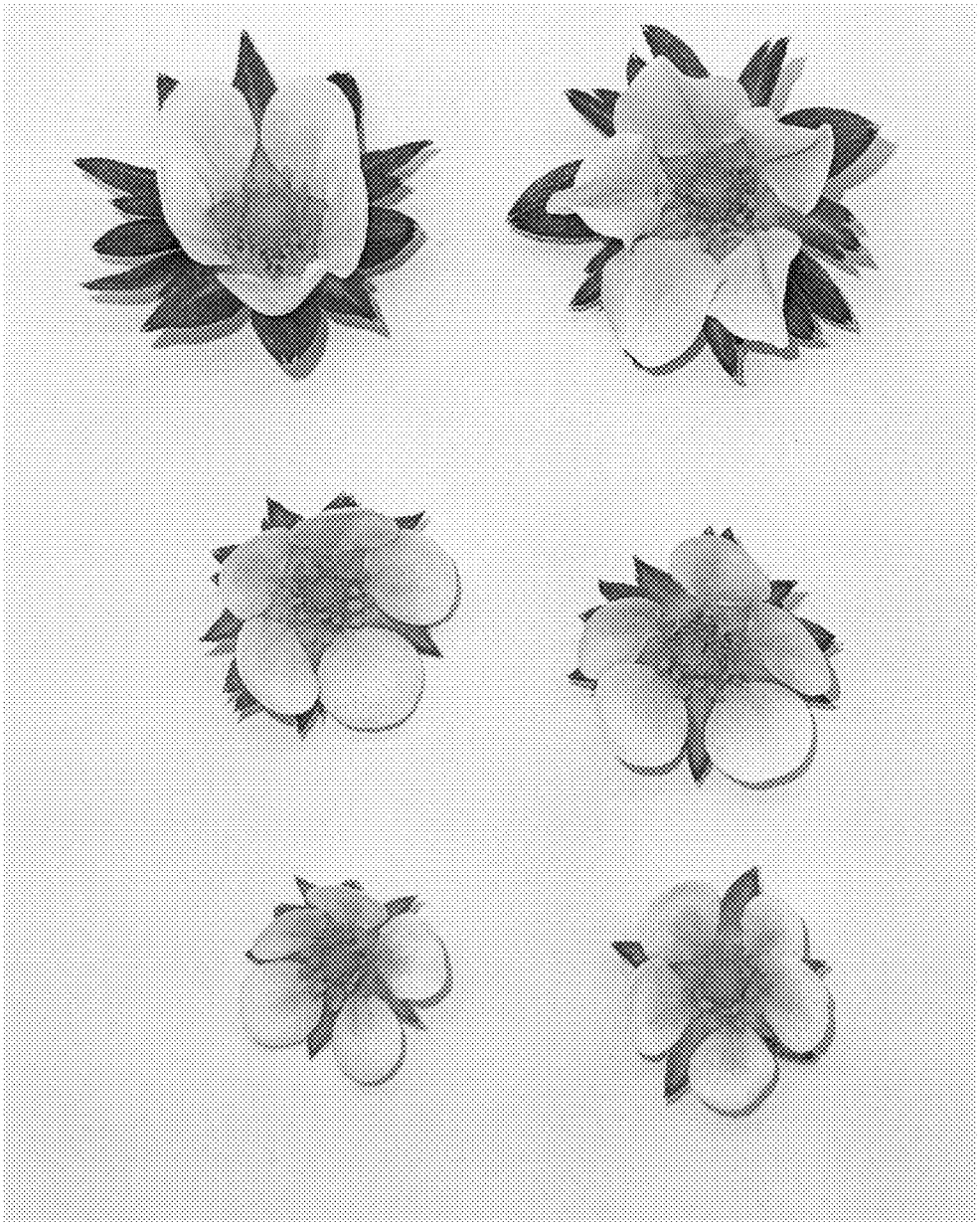

The photograph in FIG. 2 provides a close-up view of the flowers of 'AP208'.

Figure 3:
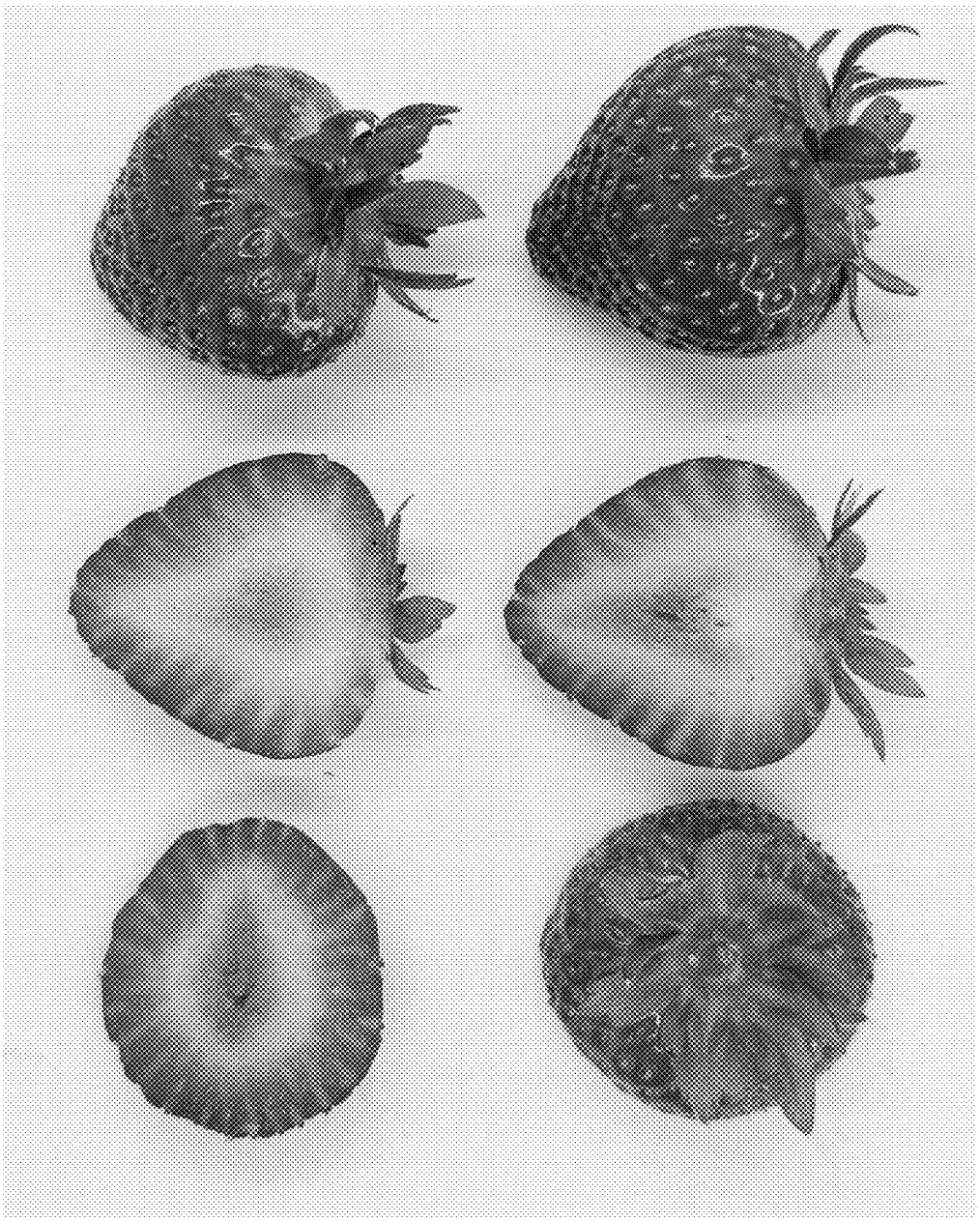

The photograph in FIG. 3 provides a close-up view of the fruit of 'AP208' (top whole fruit, middle vertical cross section, bottom horizontal cross section).

The colors in the photographs are as close as possible with the photographic and printing technology utilized and the color values cited in the detailed botanical description accurately describe the colors of the new *Fragaria*.

BOTANICAL DESCRIPTION OF THE PLANT

The following is a detailed description of 3-month-old plants (from a rooted cutting) of 'AP208' as grown outdoors on tabletops in coir bags, under polyethylene tunnels in Faversham, Kent, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Starting in April and produced throughout the Summer in Faversham, Kent, The United Kingdom.

*Plant type*.—Herbaceous fruit producing perennial.

*Plant habit*.—Semi-upright with a dense canopy and strong vigor.

*Height and spread*.—Reaches an average of 43.98 cm in height and 56.18 cm in width as a 3-month-old plant grown in a coir bag (an average height to width ratio of 1:1.2).

*Cold hardiness*.—Not tested in areas where temperatures below 32° F. occur.

*Diseases and pests*.—Tolerant to *Botrytis cinerea* and slight susceptibility to *Podosphaera leucotricha* (powdery mildew) as observed under conditions in Faversham, Kent, the United Kingdom, no susceptibility or resistance to pests has been observed.

*Root description*.—Fibrous, NN155D in color.

*Root development*.—An average of 2 weeks to initiate roots and 5 weeks to produce a young rooted plant from a rooted cutting.

*Propagation*.—Rooting of stolons and tissue culture.

*Stem description*.—Acaulescent.

*Stolon description*.—Average of 11 per plant, 5 nodes per stolon, ranging between 16.3 cm to 3.5 cm between nodes, sparsely to moderately pubescent surface, color N144D.

Foliage description:

*Leaf division*.—Compound, three leaflets.

*Leaf arrangement*.—Basal.

*Leaf attachment*.—Petiolate.

*Leaflet shape*.—Trifoliate.

*Leaf size*.—Average of 12.13 cm in length and 18.97 cm in width.

*Leaflet size*.—Terminal leaflet; average of 10.02 cm in length and 8.69 cm in width, lateral leaflet; average of 8.12 cm in length and 6.21 cm in width.

*Leaflet margins*.—Serrate to crenate, with an average of 20.4 serrations per leaf.

*Leaflet base*.—Acute.

*Leaflet apex*.—Rounded.

*Leaflet glossiness*.—High.

*Leaflet aspect*.—Mostly concave with some leaflets straight.

*Leaflet interveinal blistering*.—Absent.

*Leaflet venation*.—Pinnate, coloration matches leaflet color.

*Leaflet surface*.—Both surfaces slightly glossy, upper surface glabrous, lower surface slightly pubescent, main vein slightly pubescent.

*Leaflet color*.—Upper surface; NN137A, lower surface; 146B.

*Petioles*.—Round in shape, N144D in color, average of 26.06 cm in length and 4.18 mm in width, surface is moderately pubescent.

*Petiolules*.—Round in shape, N144D in color, average of 2.04 cm in length and 2.77 mm in width, surface weak to moderately pubescent.

*Stipule*.—Average of 2.53 cm in length and 8.9 mm in width, 48A in color.

Flower description:

*Inflorescence*.—Truss.

*Inflorescence size*.—Average of 15.66 cm in length and 27.12 cm in width, including peduncle and pedicel.

*Flower initiation and expression conditions*.—Temperature dependent.

*Time of flowering* (50% *of plants at first flower*).—Early season, commencing in April.

*Flower position relative to foliage*.—Mostly same level or beneath the leaf canopy.

*Flower size*.—2.5 cm in diameter.

*Flower number per truss*.—Average of 7 flowers.

*Flower fragrance*.—Weak-typical of species.

*Calyx*.—Average of 3.48 cm in diameter and the same size or larger in relation to the corolla, similar for primary, secondary and tertiary flowers.

*Sepals*.—Average of 11 per flower, average of 1.65 cm in length and 8.1 mm in width, obtuse base, acute apex, upper surface 141B in color, lower surface 143A in color.

*Sepal position*.—Mostly raised or level in relation to the fruit, some upwards and some outwards in attitude.

*Petals*.—5, average of 1.18 cm in length and 1.15 cm in width, obtuse base, rounded apex, touching or overlapping in arrangement, entire margins, glabrous on upper and lower surfaces, 155A in color.

*Peduncles*.—Average of 11.04 cm in length and 4.6 mm in width, 144B in color, surface strongly pubescent.

*Pedicels*.—Average of 9.59 cm in length and 2.7 mm in width, 144C in color, surface is weakly pubescent.

*Bracts*.—Observed on majority of the flowering trusses at point of branching from early developmental stage, progresses into a small single leaflet as the truss matures and the fruit develops, average of 6.05 cm in length and 2.74 cm in width, both surfaces 137A in color.

Reproductive organs:

*Gynoecium*.—Average of 3.5 mm in height and 4.9 mm in width, dome-shaped, apocarpous with multiple simple carpels present with capitate-shaped stigma.

Androecium.—Stamens; average of 22.9 per flower, anthers; average of 1.6 mm in length and 0.8 mm in diameter.

Fruit description:

*Shape*.—Mostly conical and a few cordate, similar for primary, secondary and tertiary fruit, apex of the fruit is mostly acute and calyx side of the fruit is mostly rounded.

*Season of harvest*.—May to the end of October in Faversham, Kent, the United Kingdom.

*Time of ripening* (50% *of plants with first ripe fruit*).—Early.

*Type of bearing*.—Day neutral.

*Size*.—Medium to large, average of 3.96 cm in length and 3.61 cm in width.

*Surface*.—Smooth with medium to strong glossiness.

*Calyx position*.—Mixed with some level and some upwards in relation to the fruit, similar for primary, secondary and tertiary fruit.

*Attitude of calyx segments*.—Mixed, some upwards and some outwards.

*Diameter of calyx relative to fruit diameter*.—Variable.

*Glossiness*.—Strong.

*External color* (*skin*).—N45A, color is retained throughout the cropping season.

*Internal color* (*flesh*).—158D, near margin 33B and near core 35B.

*Evenness of color of skin*.—Very even.

*Evenness of color of flesh*.—Paler near center.

*Acidity*.—0.65% TTA.

*Sweetness*.—High.

*Soluble solids*.—Average of 11.2° over three seasons in trials.

*Firmness*.—Skin is very firm (resistant to bruising), flesh is very firm.

*Juiciness*.—High.

*Aroma*.—Slight.

*Weight*.—Average of 17.4 g per berry and 1591.3 g per plant from late May to end of October over three seasons in trials.

*Number of fruit per plant*.—Average of 91.5 fruits per plant from late May to end of September over three seasons in trials.

*Hollow center*.—Slight on primary, secondary and tertiary fruit, more prominent on primary fruit.

*Shelf life*.—Good, at least 7 days in cold storage.

*Achene color*.—22A.

*Achene position*.—Majority level with the fruit surface.

*Achene number*.—An average of 250 per berry.

*Band without achenes*.—Absent.

*Market use*.—High shipping quality fruit for fresh consumption.

It is claimed:

1. A new and distinct cultivar of *Fragaria* plant named 'AP208' substantially as herein illustrated and described.

* * * * *